US008017366B1

(12) United States Patent
Schuh et al.

(10) Patent No.: US 8,017,366 B1
(45) Date of Patent: Sep. 13, 2011

(54) SELF-CONTAINED BIOFUEL PRODUCTION AND WATER PROCESSING APPARATUS

(76) Inventors: Allen John Schuh, Pleasanton, CA (US); Peter Allen Schuh, Pleasanton, CA (US)

( * ) Notice: Subject to any disclaimer, the term of this patent is extended or adjusted under 35 U.S.C. 154(b) by 224 days.

(21) Appl. No.: 12/399,323

(22) Filed: Mar. 6, 2009

Related U.S. Application Data

(60) Provisional application No. 61/052,023, filed on May 9, 2008, provisional application No. 61/051,988, filed on May 9, 2008, provisional application No. 61/051,149, filed on May 7, 2008, provisional application No. 61/050,881, filed on May 6, 2008, provisional application No. 61/049,301, filed on Apr. 30, 2008.

(51) Int. Cl.
| | |
|---|---|
| *C05F 11/08* | (2006.01) |
| *H01M 8/16* | (2006.01) |
| *C12N 1/04* | (2006.01) |
| *C12P 1/04* | (2006.01) |
| *C12P 7/04* | (2006.01) |
| *C12P 3/00* | (2006.01) |
| *C12P 5/00* | (2006.01) |
| *C12P 21/00* | (2006.01) |
| *C02F 3/28* | (2006.01) |
| *C05F 1/00* | (2006.01) |
| *C05F 15/00* | (2006.01) |
| *C12P 7/06* | (2006.01) |
| *C12P 7/16* | (2006.01) |
| *C12P 5/02* | (2006.01) |

(52) U.S. Cl. ........ 435/161; 210/603; 210/612; 210/613; 210/632; 435/41; 435/69.1; 435/160; 435/162; 435/166; 435/168; 435/170; 435/290.1

(58) Field of Classification Search ........... 210/603, 210/612, 613, 632; 435/41, 69.1, 157, 160, 435/161, 162, 166, 168, 170, 290
See application file for complete search history.

(56) References Cited

U.S. PATENT DOCUMENTS

| 4,437,937 | A  * | 3/1984 | McGraw ............... 202/160 |
| 6,299,774 | B1 * | 10/2001 | Ainsworth et al. ........ 210/603 |
| 6,667,347 | B2 | 12/2003 | O'Rear et al. |
| 7,314,503 | B2 | 1/2008 | Landrum et al. |
| 2010/0064746 | A1 * | 3/2010 | Medoff .................. 71/8 |

FOREIGN PATENT DOCUMENTS

BE 422877 B1 8/1937

OTHER PUBLICATIONS

IEI. 2006. Turnkey build operate transfer services for gas engines, power, downloaded from the internet on Feb. 12, 2011 from http://www.integratedenergyindustries.com/biogas-process.html.*
McKenna, P. From Smokestack to gas tank. New Scientist, Oct. 7, 2006, vol. 191 Issue 2572, pp. 28-29.*
Walia et al. 1994. Development of Coal Biogasification (MicGAS Process). Coal-Fired Power Systems 94—Advances in IGCC and PEBC Review Meeting Jun. 21-24, 1994. Morgantown, West Virginia, pp. 376-397.*
United States Department of Defense Design Criteria Standard, MIL-STD 1472F 23 (1999).
Archer Daniels Midland Company, "Biodiesel Technical Information", Biodiesel-Technical-Manual.pdf, www.admworld.com (2008), 12 pp.
Blume, D., "Alcohol Can be a Gas", The International Institute for Ecological Agriculture, ISBN 9780979043789 (2007), 21 pp.
House, D. "Biogas Handbook", Alternative House Information, ISBN 0-915238-47-0, AACR2 (2006), 29 pp.
Ulrich Bretscher's Wastewater Page, "Digesting Sludge and the Influence of the Temperature", http://www.musketeer.ch/sewage/thermophysic_digest.html (2008), 3 pp.
United Nations Framework Convention on Climate Change (UNFCCC) Sets Reporting Guidelines to Cover Emissions and Removals of Direct Greenhouse Gases (GHGs e.g., carbon dioxide 2008.
United States Department of Agriculture (USDA) Natural Resources Conservation Service (NRCS) Environmental Credit Trading Information Series, http://www.info.usda.gov/media/pd, May 2007.
White, D., "The Physiology and Biochemistry of Prokaryotes", Chapter 13-14, Oxford University Press (2000), 43 pp.

* cited by examiner

*Primary Examiner* — Jon P Weber
*Assistant Examiner* — Kailash C Srivastava
(74) *Attorney, Agent, or Firm* — David Pressman

(57) ABSTRACT

A system for making biofuels comprising methane, ethanol, and biodiesel comprises a tank (100) with a sealable lid (120). An algae mass (105), water, and either a yeast or bacterial culture (106) is added to the tank. Under high temperature conditions, sour ($CO_2$-containing) methane is produced and stored in a container (130). Under lower temperature conditions, ethanol and $CO_2$ are produced. Heated or cooled water passed through a water jacket (160) that surrounds the tank maintains the proper temperature within the tank. The $CO_2$ is stored in a second container (270). The sour methane and the $CO_2$ are optionally passed through a scrubber. Scrubbed methane is suitable for use as a fuel and drives a generator (275) that supplies power to various parts of the system. Carbon credits will be available for $CO_2$ that is trapped in the scrubber. A still (185) separates ethanol and water for later use. Biodiesel can also be made in the apparatus by first making ethanol, then employing a transesterification process.

16 Claims, 1 Drawing Sheet

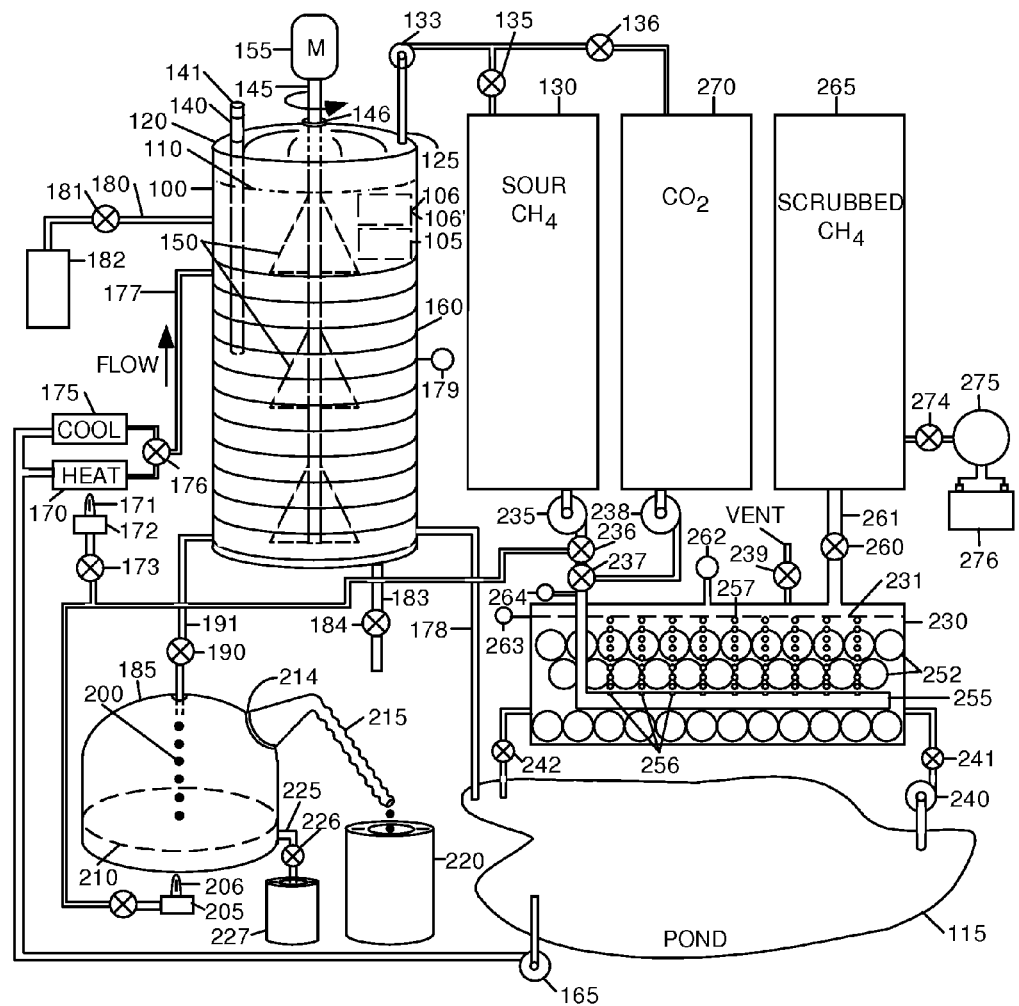

SELF-CONTAINED BIOFUEL PRODUCTION AND WATER PROCESSING APPARATUS

CROSS REFERENCE TO RELATED APPLICATIONS

This application claims priority of our provisional patent applications, Ser. Nos. 61/049,301, filed Apr. 30, 2008; 61/050,881, filed May 6, 2008; 61/051,149, filed May 7, 2008; 61/051,988, filed May 9, 2008, and 61/052,023, filed May 9, 2008. This application is related to our applications, Ser. Nos. 12/110,860, filed Apr. 28, 2008, now U.S. Pat. No. 7,591,088, issued Sep. 22, 2009, and 12/341,380, filed Dec. 22, 2008.

BACKGROUND

1. Field

The field is production and processing of biofuels.

2. Prior Art

The following is a list of some prior art that presently appears relevant:

| U.S. Pat. No. or Pub. Nr. | Kind Code | Issue or Pub. Date | Patentee or Applicant |
| --- | --- | --- | --- |
| 4,437,937 | B1 | 1984 Mar. 20 | McGraw |
| 6,667,347 | B2 | 2003 Dec. 23 | O'Rear et al. |
| 7,314,503 | B2 | 2008 Jan. 1 | Landrum et al. |

FOREIGN PATENT DOCUMENT

Belgian Patent Nr. 422,877 to C. G. Chavanne, published 31 Aug. 1937.

NON-PATENT LITERATURE DOCUMENTS

ARCHER DANIELS MIDLAND COMPANY, "Biodiesel Technical Information", Biodiesel-Technical-Manual.pdf, www.admworld.com (2008).
BLUME, D., "Alcohol Can be a Gas", The International Institute for Ecological Agriculture, ISBN 9780979043789 (2007).
HOUSE, D. "Biogas Handbook", Alternative House Information, ISBN 0-915238-47-0, AACR2 (2006).
ULRICH BRETSCHER'S WASTEWATER PAGE, "Digesting Sludge and the Influence of the Temperature", http://www.musketeer.ch/sewage/thermophysic_digest.html (2008).
United Nations Framework Convention on Climate Change (UNFCCC) Sets Reporting Guidelines to Cover Emissions and Removals of Direct Greenhouse Gases (GHGs e.g., carbon dioxide and methane) Data Reported by Countries That Are Parties to the Climate Change Convention", http://unfccc.int/2860.php (2008).
United States Department of Agriculture (USDA) Natural Resources Conservation Service (NRCS) Environmental Credit Trading Information Series, http://www.info.usda.gov/media/pdf/NB_190_7_a.pdf (2008).
United States Department of Defense Design Criteria Standard, MIL-STD 1472F 23 (1999).
WHITE, D., "The Physiology and Biochemistry of Prokaryotes", Chapter 13-14, Oxford University Press (2000).

All of the above references show apparatuses and methods of producing or enhancing the production of fuels from biological materials; such fuels are known as biofuels. Any increase in production of such biofuels is important in today's world because of dwindling oil supplies and the inadequacy, dangers, or costs of alternative sources of energy.

McGraw, supra, shows a distillation unit for producing hydrated alcohol from a fluid mixture containing alcohol. McGraw uses more energy than necessary to accomplish the result because his system fails to isolate the features that need heat from those that need to remain cool. Also the length and configuration of the distillation unit is either not shown or is suggested to be larger and longer than necessary. In fact the prior art as a whole assumes a typically tall (long) distillation column is needed for cooling the heated liquids, but it is not separated with thermal barriers from that which needs to remain hot to accomplish the task of evaporation. Thermal isolation has been lacking. McGraw does not allow the fast micro-adjustment of temperature during operations. Also his apparatus is larger and more complicated than necessary, especially when operated in remote field settings where operation, maintenance, repair, and obtaining spare parts are problematic.

O'Rear et al., supra, show a method for removing carbon dioxide ($CO_2$) from a gas stream that contains methane and $CO_2$.

Landrum et al., supra, show a process to remove nitrogen and/or carbon dioxide from methane-containing streams.

O'Rear and Landrum's apparatuses are complex, expensive, and cumbersome compared to what can be accomplished in a simpler direct process.

MIL-STD-1472 is acknowledged worldwide as the authoritative source for human factor requirements and design criteria for the safe operation and maintenance of equipment. This standard is often referenced by government agencies, contractors, and other nations. Most Department of Defense acquisition programs now require the prime contractor to provide a human engineering data document that describes in detail how human engineering will be incorporated into the development effort. A significant part of the effort is the MIL-STD-1472 (human factors guidance) tailored checklist. This ensures that human engineering is a significant part of the system to protect the safety and health of workers. Compliance to standards work is not a casual activity; it requires a serious commitment as well as an investment of time and resources. The use of MIL-STD-1472 insures consistency and compatibility across systems. Heretofore, insofar as we are aware, no biofuel production system addresses this requirement or how to arrange the operation and maintenance features of the equipment to conform to this standard.

In the past, ethanol was commonly produced as a biofuel by fermentation of feedstock materials. However the yield or efficiency of production was low or unknown since it was difficult to control dynamically the nutrition and pH of the fermentation environment during fermentation. Also the use of ethanol created problems since some governments require that ethanol be used only as a fuel, not for human consumption. Additionally, some require that its production be strictly monitored and that it be denatured before being released for non-consumption purposes. Governments often require either the production of denatured ethanol or that the consumable ethanol be strictly regulated and taxed.

Another related problem was that carbon dioxide ($CO_2$) produced during the processing of biofuels was released into the air. Because of this, carbon credits were not available to biofuel producers as a separate income stream.

Another problem related to the present area was that, insofar as we are aware, algae has been widely available, but it was regarded as a nuisance and large sums were spent to remove and discard it. E.g., many ponds and lakes had large growths of algae that rendered the body of water unusable for recreation or drinking so it had to be removed periodically and discarded, an expensive and time-consuming process.

SUMMARY

A digesting apparatus makes the production of biofuel more economically feasible by reducing the space and time required for biofuel production. Important fuels like biodiesel, methane, and ethanol are produced from algae, in a single container, by the regulation of internal biologically friendly environmental conditions specific to the fuel production requirements, including internal temperature and pH. These factors make it possible to optimize the levels of a very specific biofuel production. One embodiment uses only self generated power, i.e., it achieves true energy self sufficiency. According to one aspect, the three kinds of fuel and potable water are produced in a single modularized unit that can be transported to remote settings. The apparatus is simple and logical in construction, utilizes self-generated fuel, and important human engineering principles for operation and maintenance of the apparatus in a safe manner by a single person. For a better understanding, see the following description in conjunction with the accompanying drawing.

DRAWING FIGURE REFERENCE NUMERALS

| | |
|---|---|
| 100 | Container |
| 105 | Algae cake |
| 106 | Bacteria Culture or Yeast Cake |
| 110 | Reactants Level |
| 115 | Pond |
| 120 | Lid |
| 125 | Methane and $CO_2$ Conduit |
| 130 | Sour Methane Container |
| 133 | Methane and $CO_2$ Pump |
| 135 | Sour Methane Inlet Valve |
| 136 | $CO_2$ Valve |
| 140 | Tube |
| 141 | Airlock |
| 145 | Shaft |
| 146 | Seal |
| 150 | Paddle |
| 155 | Motive Source |
| 160 | Blanket |
| 165 | Cooling and Heating Water Pump |
| 170 | Heat Exchanger |
| 171 | Water Heater Flame |
| 172 | Water Heater Burner |
| 173 | Heater Methane Valve |
| 175 | Cooling Station |
| 176 | Cooling and Heating Water Valve |
| 177 | Cooling Water Inlet Conduit |
| 178 | Cooling Water Exit Conduit |
| 179 | Temperature Sensor |
| 180 | Biodiesel Conduit |
| 181 | Biodiesel Outlet Valve |
| 182 | Biodiesel Container |
| 183 | Outlet |
| 184 | Container Drain Valve |
| 185 | Still |
| 190 | Still Inlet Valve |
| 191 | Ethanol and Water Conduit |
| 200 | Droplets |
| 205 | Still Burner |
| 206 | Still Heater Flame |
| 210 | Water |
| 214 | Connector |
| 215 | Tube |
| 220 | Ethanol Container |

-continued

| | |
|---|---|
| 225 | Water Conduit |
| 226 | Still Drain Valve |
| 227 | Water Container |
| 230 | Scrubber |
| 231 | Scrubber Water Level |
| 235 | Sour Methane Pump |
| 236 | Sour Methane Outlet Valve |
| 237 | Scrubber Inlet Valve |
| 238 | $CO_2$ Pump |
| 239 | Scrubber Vent Valve |
| 240 | Scrubber Water Pump |
| 241 | Scrubber Water Inlet Valve |
| 242 | Scrubber Water Outlet Valve |
| 252 | Calcium Carbonate |
| 255 | Bubbler Tube |
| 256 | Holes |
| 257 | Bubbles |
| 260 | Scrubbed Methane Valve |
| 261 | Scrubbed Methane Conduit |
| 262 | $CO_2$ Sensor |
| 263 | Level Sensor |
| 264 | Sour Methane $CO_2$ Sensor |
| 265 | Scrubbed Methane Container |
| 270 | $CO_2$ Container |
| 274 | Generator Methane Valve |
| 275 | Engine and Generator |
| 276 | Battery |

DESCRIPTION

As stated, algae is plentiful in many bodies of water, but was considered a nuisance and expensive to remove and discard. However we have discovered that such algae can be utilized for productive purposes and that there are numerous payoffs available to the harvester of algae. Algae contains at least three energy-bearing components: lipids within the algae cell structures can be collected and converted into oil used in the production of biodiesel, carbohydrates in the cell structures can be collected and converted into ethanol, and methane gas can be obtained from the residue not consumed in the biodiesel and ethanol reactions. The methane gas can be stored or burned immediately as a fuel to provide heat or supplied to an internal combustion engine to power various kinds of equipment such as electrical generators.

An apparatus according to one aspect of the one embodiment produces biofuel components from algae in an efficient manner. Different environmental conditions are used to create conditions that optimize the production of specific biofuel components at different stages. These components include biodiesel, ethanol, and methane.

The drawing shows a schematic view of the components that comprise the apparatus according to one aspect. This apparatus is capable of producing methane, ethanol, biodiesel, and potable water from algae. The main components of the system are a main reaction tank or feedstock container 100, a plurality of storage containers 130, 270, and 265 for storing sour methane (i.e., methane that is contaminated with $CO_2$ and other gases), scrubbed methane, and $CO_2$, a still 185 under reaction tank 100, and a scrubber 230 under storage containers 130, 270, and 265. These various components are interconnected by a plurality of conduits, valves, and pumps, which will be discussed in detail.

Feedstock container 100 holds a mixture of reactants and reaction products. The temperature within tank 100 is monitored by a temperature sensor 179. The reactants include an algae cake 105 and water up to a level 110 that is derived from a local source such as a pond 115. Cake 105 is inserted into the water in tank 100 and is shown initially near level 110. However cake 105 soon dissolves, so that the algae disperse throughout tank 100. Cake 105 is formed in a previous process (not shown) and is the end result of a dredging or filtering operation in which an algae mass is separated from water and partially or completely dried. The reaction products include methane, ethanol, and biodiesel. Potable water is a byproduct that is separated from the other reaction products.

Container 100 has a sealed, domed lid 120. A conduit 125 connects lid 120 to a storage container 130 that receives sour methane gas via a valve 135. A sampling and adjusting tube 140 passes through lid 130 and extends about halfway down container 100. The top end of tube 140 includes an air lock 141 that lets air out of container 100 but will not let any air in, thereby to exclude oxygen from tank 100 during operation. Airlock 141 can be a seal made of overlapping flexible membranes, a self-healing puncturable material, an iris, or the like. A shaft 145 with attached paddles 150 comprises a mechanical stirrer and is rotatably mounted in container 100 and passes out through lid 120 via a gas-tight seal 146. Shaft 145 is connected to a motive source or motor 155. Motive source 155 can periodically turn shaft 145 and can be a hand crank, electric motor, internal combustion engine, water wheel, wind-powered motor, or the like.

Container 100 is wrapped with a thermal blanket 160. Blanket 160 preferably comprises a set of tubes through which hot or cold water can be passed in order to maintain a predetermined temperature within container 100. A pump 165 supplies water from pond 115 to a heat exchanger 170 and a cooling station 175. Cooling station 175 can be cooled by an evaporative spray or other means (not shown), or simply by passage through of water from pond 115. Heat exchanger 170 is heated by a flame 171 from a burner 172. Burner 172 can burn sour methane from container 130 or scrubbed methane from container 265, or gas from another source. Alternatively, burner 172 can be replaced by a resistive electric heater (not shown), or a source of solar or geothermal heat (not shown). A valve 173 adjusts the flow of gas to burner 172. Water exits heat exchanger 170 or cooling station 175 via a proportional valve 176. Valve 176 is arranged to pass either heated or cooled water or a mixture of the two to blanket 160 via a conduit 177. The water passing through blanket 160 exits via a conduit 178 and is returned to pond 115.

A conduit 180 connected to tank 100 permits removal of biodiesel from tank 100 via a normally closed valve 181 after the various chemical reactions, described below, are complete. The biodiesel is temporarily stored for later use in a container 182.

A still 185 is connected via a valve 190 and conduit 191 to the lower portion of container 100. Opening valve 190 permits a fine stream or droplets 200 of an ethanol-water mixture to enter still 185. The bottom of still 185 is heated by a burner 205 having a flame 206. Burner 205 preferably burns gas from the same source as burner 172, although another source can be used. Alternatively burner 205 can be replaced by an alternative heat source such as solar heat, geothermal heat, heat from a resistive heating element, or the like. When droplets 200 strike either the bottom of still 185 or the surface of heated water 210, the ethanol in droplets 200 vaporizes, leaving behind water 210. The ethanol vapor leaves still 185 via a condensing tube 215 where the ethanol vapors are cooled and condense into ethanol liquid. A thermally isolating connector 214 joins column 215 to still 185. This improves the efficiency of still 185 and condenser tube 215 since still 185 is hot and tube 215 must remain relatively cool. Under the action of gravity, the liquid ethanol leaves tube 215 and flows into a container 220 for temporary storage and later use. Water 210 is removed from still 185 via conduit 225 and valve 226 and stored in a container 227 for temporary storage and later use.

Container 130 is connected to a scrubber unit 230 via a pump 235 and a two-way valve 236. Scrubber 230 is filled with water pumped by a pump 240 from pond 115 to a level 231, leaving a gap between level 231 and the top of scrubber 230 as required. A level sensor 263 optionally comprises a sight glass, a float valve, or a switch for deactivating pump 240 when level 231 is reached. A pair of valves 241 and 242 are connected to scrubber 230 by conduits and are opened when pump 240 is energized for changing the water in scrubber 230. Scrubber 230 contains pieces of calcium carbonate material 252 that are preferably about 10 mm in diameter. A bubbler tube 255 with a series of holes 256 extends from valve 236 into scrubber 230. When valve 236 is open and pump 235 is activated, methane present in container 130 is urged to pass through holes 256 and bubble upward into the open space above water level 231, as indicated by bubbles 257. When opened, another valve 260 permits methane gas to leave scrubber 230 and enter storage container 265 via a conduit 261. A $CO_2$ sensor 262 is arranged to detect the amount of $CO_2$ contained in the volume of gas between level 231 and the top of scrubber 230. An additional $CO_2$ sensor 264 detects the amount of $CO_2$ contained in the sour methane as it enters scrubber 230.

$CO_2$ container 270 is connected to tank 100 via conduit 125 and valve 136. Container 270 is used to store $CO_2$ gas when it is produced in tank 100 and valve 136 is open. $CO_2$ gas present in container 270 can also be scrubbed by scrubber 230. A two-way valve 237 conducts $CO_2$ gas from container 270 to scrubber pipe 255 via an optional pump 238. Pump 238 is not required if container 270 is a gas bag with sufficient elasticity to expel $CO_2$ through valve 237 when valve 136 is closed. A valve 239 is located on the top of scrubber 230. Valve 239 is normally closed when scrubbing $CO_2$ gas. The amount of $CO_2$ captured by carbonate 252 is eligible for $CO_2$ credits.

An internal combustion engine and generator 275 are driven by scrubbed methane from container 265. A battery 276 serves to start generator 275 when it is to be used, and also to store energy for driving other electrical apparatus such as motive source 155, and pumps 133, 165, 235, 238, and 240.

In one embodiment the volume of tank 100 was about 2,000 liters and the volumes of containers 130, 265, and 270 were about 10,000 liters, but obviously other size containers can be used.

Unless otherwise indicated, all pumps and valves are certified explosion proof. The unit is designed with high regard for human engineering principles, namely operation and maintenance, including health and safety. In the embodiment shown, each transfer of liquid is accomplished by a dedicated pump.

Operation in General

The apparatus is multi-purpose, i.e., two different results can be obtained from the same feedstock and same apparatus, depending upon the conditions within tank 100. Under a first set of conditions with the addition of bacteria to the feedstock, methane and $CO_2$ are produced. Under a second set of conditions with the addition of yeast to the feedstock, ethanol and CO2 are produced.

The methane ($CH_4$) and carbon dioxide ($CO_2$) produced in tank 100 pass outward through conduit 125 in lid 120. When methane is produced and valve 135 is open while valve 136 is closed, sour methane, which includes $CO_2$, is conveyed to container 130. When ethanol is produced and valve 136 is open while valve 135 is closed, $CO_2$ is conveyed to container 270.

For each of the above reactions, the temperature within tank 100 is monitored by temperature sensor 179. The chemical conditions, nutrient levels, pH, and level of water within tank 100 are monitored by withdrawing samples through tube 140. Care is taken to prevent the introduction of oxygen to tank 100 during these operations. All these conditions are maintained within predetermined tolerances as the chemical reactions proceed. In the event the contents of tank 100 require an increase in temperature, pump 165 and burner 172 are activated while valve 176 regulates the temperature of water being urged to flow from heat source 170 and through blanket 160. Alternatively, in some instances the contents of tank 100 require cooling, in which case flame 171 on burner 172 can be lowered or extinguished and valve 176 can be adjusted to deliver cool water from source 175.

The temperature within tank 100 can be controlled manually by an operator, or automatically by a known temperature control system (not shown). It is desirable to maintain the temperature to within a tolerance of 2° C. The contents of tank 100 require heating to about 50° C. for methane production. On the other hand, the temperature of the contents of tank 100 are optimally about 32° C. for the production of ethanol. When mixing the materials used in the biodiesel production operation, a temperature between these two will be appropriate. The ability to regulate the heat of the container contents is critical for optimum fuel production.

Production of Sour Methane

For the first stage of sour methane operations, lid 120 is temporarily opened and an algae cake 105 is added to tank 100. Sufficient water is added to tank 100 to cover cake 105 and form a slurry when stirred by paddles 150. In addition, water is added up to level 110, near the top of tank 100 so as to purge the system substantially of oxygen. The appropriate seed bacteria 106, for example a culture comprising a variant of the genus *Methanobacterium* (found in mud, sewage, sludge, and in the rumen of sheep and cattle) or a well known and widely available septic tank seed culture, are also added to the biomass-water combination in order to start the breakdown of the algae in cake 105. Lid 120 is then closed. Next, valve 135 is opened to permit gases generated within tank 100 to move into gas storage container 130. Valve 136 remains closed in order to exclude methane from container 270. The generation of sour methane commences immediately. The rate of generation is optimized by selecting a temperature that is predetermined to maximize the growth rate of the bacteria in culture 106. Pump 133 is optionally activated to overcome back pressure from tank 130 as it is filled.

The temperature to be maintained within tank 100 for this process is approximately 50° C., although with some seed bacteria (cake 106) the optimal temperature will be higher (Ulrich Bretscher, supra). The required temperature range is maintained by a human operator (not shown) who either employs automatic means (not shown) or regulates the system manually. The required heat is provided by opening valve 173 and activating burner 172. Pump 165 is also activated, drawing water from pond 115, and valve 176 is adjusted to cause the flow of water heated in heat exchanger 170 to pass through conduit 177 and blanket 160. Thereafter the water exits blanket 160 via conduit 178 and returns to pond 115. The sour methane gas is collected in container 130 on a continuous basis from the moment lid 120 of tank 100 is sealed. The rate of production of sour methane gradually accelerates, peaks, and then declines over the period of a few hours. Motive source 155 can be periodically activated in order to cause paddles 150 to stir the contents of the tank and optimize methane production. This first stage process of sour methane capture is allowed to continue until the operator determines that there has been sufficient breakdown of algae cell walls, thereby exposing the carbohydrates within the algae for the next stage of operations. The determination is aided by withdrawal and inspection of the contents of tank 100 via tube 140.

The sour gas is carried by pump 133 to container 130 for temporary storage. The sour gas is then sent by pump 235 to either burner 172, burner 205, or scrubber 230, depending upon the direction of flow determined by two-way valve 236. In this operation, valve 237 is oriented so that sour methane gas flows to scrubber pipe 255. If sent to scrubber 230, the sour methane gas is released through holes 256 in bubbler tube 255 and collects in the space between water level 231 and the top of scrubber tank 230.

Purifying Sour Methane by Scrubbing

When it is desired to purify the sour methane in container 130, it is passed through scrubber 230 and collected in container 265. This is accomplished by activating pump 235 and directing the flow of sour methane through valve 236 into bubbler tube 255 within scrubber 230. When the sour-gas is being pumped by pump 235 into scrubber 230, valve 260 is open. When pump 235 stops, valve 260 is closed. Valve 260 and pump 235 can be manually operated by an operator, or their operation can be automated.

$CO_2$ is removed from the sour methane gas by simple absorption by calcium carbonate material 252 and surrounding water. The absorption is reversible. $CO_2$ that has been absorbed by calcium carbonate can be removed by rinsing the calcium carbonate in water that contains little or no $CO_2$. Alternatively, the $CO_2$ can be removed by exposing the calcium carbonate to heat and air.

$CO_2$ sensor 262 reports the amount of $CO_2$ in the gas volume between level 231 and the top of scrubber 230. The decision whether to use or to clean scrubber 230 is determined by the operator. The efficacy of scrubber 230 varies at least according to the amount of $CO_2$ already absorbed by calcium carbonate 252 from previous scrubbing operations, the amount of $CO_2$ in the gas being scrubbed, the quality of calcium carbonate 252, and the temperature of the water in the scrubber. The difference between the amount of $CO_2$ in the sour gas entering the scrubber and the amount of $CO_2$ in the scrubbed methane leaving the scrubber is compared with a predetermined criterion in order to determine whether to purge the $CO_2$ from calcium carbonate 252. For example, if the sour methane entering scrubber 230 contains 35% $CO_2$ and the scrubbed methane gas entering container 265 contains 25% $CO_2$, then scrubber 230 has removed 10% of the $CO_2$ present in the sour methane. At this point, calcium carbonate 252 is partially loaded with $CO_2$ so it will remove less $CO_2$, say 5%, in the next operation. It is economically desirable to remove as much $CO_2$ as possible from the sour methane since the removed and sequestered $CO_2$ can be tabulated for carbon credits.

When scrubber 230 removes less than a predetermined amount of $CO_2$ from the incoming gas stream, it must be shut down and purged. This is done by deactivating pump 235, and closing valves 236 and 260. Next, valves 241 and 242 are opened and pump 240 is activated. While pump 240 is activated, water from pond 115 is pumped through scrubber 230 and circulates among calcium carbonate chunks 252, absorbing and removing the $CO_2$ that has been adsorbed. The removed $CO_2$ enters pond 115 where it is available to algae and other growing plants. After the purging operation, valve 242 is closed and pump 240 continues to operate until level sensor 263 indicates that level 231 has been reached. At that point, pump 240 is deactivated and valve 241 is closed. The scrubber 230 is now in condition to continue operation.

Instead of purging scrubber 230 with water, carbonate chunks 252 can be removed from scrubber 230 and allowed to bake in the sun, whereupon the adsorbed $CO_2$ will be driven off into the atmosphere.

The scrubbed methane stored in container 265 can be used in a variety of ways, including powering internal combustion engines, fuel cells, burners, and the like.

A second methane extraction can proceed after an intermediate ethanol fermentation stage (described below) is completed. Additional replacement water can be added to the contents of tank 100 if required. This second methane production stage may last as little as two days. The methane generating conditions at this later stage may be different than in the initial stage of cell breakdown, i.e. a different operating temperature may be required for optimum functioning of the different strain of seed bacteria added for this phase that converts the remaining mass to methane. Any residual biomass cake remaining in the main unit after all biofuel production operations are complete can be removed for use in agricultural operations typically to the feedstock pond to meet the nutritional needs of the next generation of algae.

Production of Ethanol

The production of ethanol follows the production of methane and uses the algae mass that has been largely stripped of the algal cell walls during methane production. For this stage of operations, an alcohol yeast 106' (*Saccharomyces cerevisiae* variant), is added to tank 100. The production of ethanol is a relatively low-temperature operation. The contents of tank 100 must be kept at about 30° C. To maintain the temperature range necessary for the proper operation of the apparatus during the production of ethanol, it may be necessary to cool or shade the unit at times.

Tube 140 for sampling and adjusting the internal environment of tank 100 is an important feature of this apparatus. Tube 140 extends through airtight lid 120, through the space between level 110 and lid 120, and about half-way down into tank 100. The water-nutrient-pH adjusting augmentation is accomplished through tube 140. The chemical, nutrient levels, pH, amount and condition of water, are monitored through tube 140 in order to maintain the reactions within tank 100 within tolerances. Each strain of yeast performs best at a particular, known pH value. The pH value in the reaction chamber must be maintained at this value for the yeast to thrive and the fermentation to proceed optimally. Acid materials such as lemon juice, vinegar, and the like can be added to the reaction tank when the pH is too high for a particular strain of yeast. Basic materials, such as potash, can be added when the pH is too low.

$CO_2$ liberated during the production of ethanol is collected in container 270. Valve 135 is closed, valve 136 is opened, and pump 133 is activated if necessary to move the $CO_2$ from tank 100 to container 270.

After sufficient reaction time, perhaps two days, when the ethanol production is judged by the operator to be substantially completed, pump 133 is stopped, valve 136 is closed, and lid 120 can be lifted for visual inspection of the fluid level and its nature, i.e., the percent ethanol in the water-algae mixture.

After the ethanol generation process, still 185 is used to separate the components comprising the ethanol-water mixture. To commence operation of still 185, burner 205 is activated and flame 206 heats the bottom of still 185. When the bottom of still 185 reaches the desired operating temperature (between 78° and 100° C.—electronic temperature gauge not shown), valve 190 is opened, permitting droplets 200 of the water-alcohol mixture to enter still 185. This operating temperature is maintained by adjustment of valve 173 as it affects the size of flame 206 and valve 190 as it affects the rate of fall of droplets 200. When droplets 200 strike either the heated bottom of still 185 or the top of heated water layer 210, which accumulates during the operation of still 185, the ethanol immediately evaporates, leaving liquid water behind. During evaporation, the ethanol vapors create a positive partial pressure within still 185. This urges the vapors to leave still 185 via the opening provided through condenser 215. The ethanol vapors return to a liquid state as they are cooled in condenser 215. The distilled ethanol drips out of condenser 215 and is collected in a temporary storage container 220. During operation of still 185, the operator periodically opens valve 226, permitting water to be collected in temporary storage container 227.

Flash evaporator still 185 releases the ethanol as a vapor from the water-ethanol mixture urged by two properties of the mixture. Ethanol has a lower boiling point than water and it has also a lower requirement for phase-change energy, sometimes referred to as the latent heat of vaporization. A one-half meter long ribbed tube of this apparatus has a 30 mm internal diameter but it can extract six times the rate as a smaller 15 mm smooth length of copper coil typically used.

From 2,000 liters of algae feedstock, as in this example, at least 20 liters of ethanol can be produced. Alcohol yield can be monitored by a human operator using a test instrument.

If the algae are not healthy and well fed, ethanol recovery can be skipped entirely to maximize the recovery of methane. This choice would normally depend on economic conditions.

During the precipitation of alcohol on the wall of the distillation device, the operator can optionally denature the alcohol so that it will be useable as fuel exclusively and unfit for human consumption. In some locals, legal, tax, and social reasons are advanced to render the alcohol suitable for use as fuel only at this point. One mechanism that can be used to denature the ethanol is a metal, such as aluminum, in condenser 215. (Stainless steel or copper will not denature the alcohol.) By denaturing the alcohol at the point where it is precipitated, there it will not be possible to misuse it for human consumption. Fuel made by this apparatus can be processed in geographical areas where because of religious observance or civil ordinances, the manufacture of alcohol for human consumption is forbidden. According to the regulations governing the production of alcohol as a fuel, a denaturing agent must be added to prevent its misuse, according to regulations of the U.S. Government Department of Alcohol, Tobacco, and Firearms. Using the apparatus of this construction makes that procedure automatic.

Production of Biodiesel

For the production of biodiesel from the lipids in the algae mass, the first step is to make ethanol. Yeast cake 106' is added to the feedstock in tank 100 and fermentation converts the naturally-occurring sugars from the carbohydrates in the algae to ethanol. After ethanol production, the naturally-occurring algae oils, also called lipids, not removed by any earlier procedure remain in tank 100 and the ethanol is fermented in situ, to which only the acid need be added to start the transesterification process. During ethanol production by fermentation of the algae feedstock, the problem mentioned earlier was the acid buildup of the contents, which left unchecked would kill the yeast. In maximizing ethanol production it was necessary to adjust the pH to neutral continuously to maximize production of the conversion of all sugar to ethanol. Now, however, it is beneficial for the production of the biodiesel to allow the acid level to build up and not correct it to neutral by adding a base. The tradeoff is less ethanol but usually there will be no need to add supplementary acid. In the container where the ethanol is fermented, the conditions are correct for immediate transesterification, (i.e. the process of exchanging the alcohol group of an ester with another alcohol). Ethanol is used in order to separate the fatty acids from the glycerol by replacing the glycerol with short linear alcohols because it is an acid environment in the presence of whatever oil is present in the lipids of the algae alongside the ethanol. As a guide, the ethanol will be in about the right proportion to the lipids to be converted to biodiesel. As mentioned, if necessary, additional waste materials, which are acidic, such as old wine spoiled to become vinegar, can also be used to increase the acidity of the mixture. During this process, the contents of tank 100 is heated and stirred.

Then follows a base catalyzed transesterification. The base material is added, stirred, and heated. There are base materials, such as ashes of wood fires, that are considered as waste products. The ashes of wood fires, especially from broadleaf hardwoods, has been used to make lye and potash since historic times.

After the addition of the base material, this leaves ethyl esters, glycerin, and trace contaminants. Either before or after removal of the glycerin, the biodiesel is removed through outlet 180 and valve 181 to a suitable storage unit 182. The glycerin is removed by drainage through sump outlet when valve 184 is open, thereby leaving the ethyl esters and trace contaminants in tank 100.

Any material remaining in the processor after the biodiesel is removed is acceptable for immediate reuse in agricultural operations, i.e. for soil enrichment, or it can be dried, pelletized, and burned as an alternative fuel source. If burned it may be a modest source of potash for use in a later biodiesel production or the production of cinder blocks for local construction projects. The remaining material can also be returned to the feedstock source pond to assist in meeting the nutritional standards of the next generation of feedstock.

The apparatus can be designed to accommodate any size facility or plurality of facilities, or to treat a plurality of agricultural materials. Using the guidelines provided herein, and given the predicted amount of agricultural material to treat, those skilled in the art are capable of designing a suitable system described.

Review and Other Considerations

The methane can be produced at more than one stage of the process. The first methane recovery step described below can be skipped if in the processing of the feedstock algae there was an oil extraction from the biomass. In an oil extraction procedure, the cell walls would have been substantially destroyed in the process that separated the oil from the algae oil-less cake. The primary purpose of a first methane digestion is to break down cell walls. If that procedure were accomplished by bio-oil extraction, the producer could then move directly to ethanol production, if desired.

The process of methane production in the apparatus described below takes place in the same reservoir that can produce ethanol. This can be done by the application of predetermined temperatures and the regulation of other internal environmental conditions such as the adjustment of pH, water, and nutrient levels. Seed bacteria are added in the case of methane, versus seed yeast in the case of ethanol. Since either methane or ethanol can be produced from the feedstock, the proportions can be determined by management's production needs at the time. Thus the fuel produced can be chosen as either fluid for wheeled transportation or gas for heating or electrical generation. Both types of fuel can be derived from the same feedstock in a single apparatus.

In the production of ethanol, the starting materials remain at a desirable temperature for maximum yeast conversion of the sugars to ethanol for a particular yeast strain. The mechanism of ethanol production is a result of fermentation. The amount of alcohol that can be produced from fermentation of simple sugars, in a water solution, and with a strain of yeast, can be limited from achieving its theoretical maximum for the yeast strain by the changing pH, water level and character, temperature, nutrient, and other chemicals in the environment during the process. Thus the ideal internal environment for the optimum production of ethanol at any point in the process is best adjusted on a dynamic basis.

The fermentation process must exclude oxygen. If oxygen is present, yeast undergoes aerobic respiration, which produces carbon dioxide and water rather than ethanol. When certain species of yeast, most importantly, *Saccharomyces cerevisiae*, metabolize sugar ($C_6H_{12}O_6$) in the absence of oxygen, they produce ethanol ($CH_3CH_2OH$, alternatively $C_2H_5OH$) and $CO_2$. Ethanol's toxicity to yeast limits the ethanol concentration obtainable in a static environment. The most ethanol-tolerant strains of yeast can survive up to approximately 15% ethanol by volume although higher yields are theoretically possible. As long as limiting thresholds are not approached, the yeast will produce its theoretical maximum. At present, the limiting threshold is not known. Augmenting the internal environment by supplementing with appropriate adjustments without contaminating the contents of the fermentation/digestion container is an important feature of the apparatus. Constant sampling and the micro-adjustment necessary to maintain the ideal growing environment should yield substantially higher ethanol production from a given amount of feedstock than has been possible in prior art without this adjustment ability.

The ethanol resulting from fermentation is then evaporated and distilled from its water medium in an atmospheric distiller operation, in a continuous process, utilizing as a heat source the methane currently or just previously produced by the same apparatus. Typical batch evaporation techniques require the heating of the entire mixture to be distilled to a temperature above the boiling point of its contents. The vapor then passes to a distillation device to collect the precipitated alcohol, which can contain at least some trace of water, but in a greatly reduced amount compared to the preheated mixture. Blume, supra, suggests that multiple passes through the device may be necessary if the result is to be used as a fuel in an internal combustion engine. The devices which provide evaporation and distillation need not be sophisticated because ethanol reaches its boiling point before water does. Ethanol has also a lower requirement for phase-change energy, the energy required to change the liquid to a gas, sometimes referred to as the latent heat of vaporization. A well known problem with batch distillation is that the dynamic changes in alcohol proportion of the batch changes the boiling point of the total mixture and in turn the production quality of the resultant alcohol and water mixture. An advantage of flash evaporation is the steady state of conditions for that evaporation. With drop-by-drop continuous burst evaporation, as in the apparatus described below, exactly the same conditions for evaporation exist from the first to the last drop from the fermentation unit or the ethanol-water temporary holding tank between the fermentation tank and the evaporation device.

The evaporation-distillation apparatus is capable of producing ethanol in a simple, safe, and highly economical manner in a continuous rather than batch process. When evaporating and distilling ethanol from algae, the alcohol content of the sample can vary widely. It may be as little as one or two percent in some samples, which is the lowest level often where most batch distillation ends its run. In centralized commercial settings, this low alcohol content is often not worth processing, but in the extraction of alcohol from algae in a remote field setting, that may be the highest percentage alcohol the particular sample achieves for the wild pond strains in that geographical location. Even low-grade yields are valued in remote settings where there is not an alternative but to process what ever is available. Put another way, this apparatus can perform its operations with low-yield samples.

Ideally, the continuous flash evaporator uses the lowest possible energy to achieve the production required. The energy required to operate the evaporation can be derived from the system that created the fuel. The use of heat resistant connectors, such as those made from glass, ceramic, or other insulation, separate the parts of the apparatus to prevent heat from the evaporation unit traveling beyond its point of greatest usefulness. This isolation of where the thermal energy is expended, is seen as a desirable feature of this apparatus that, to our knowledge, has not been addressed. Usually, everything, including the column used as a distillation condenser, which becomes a heat sink, is heated by the thermal unit, as is the evaporator, thus wasting energy and even working at cross purposes with the distillation portion of the apparatus. In one aspect of this embodiment, heat-resistant connectors separate all places where heat is desired from where it is not desired. To minimize the expense of fuel to run the operation, and to maximize the efficiency of the distillation portion of the apparatus, the evaporation and distillation portions of the device need to be small, specialized, and thermally isolated. By virtue of thermally isolated connections, portions of the apparatus that are heated are thermally separated from those that should remain cool. In another aspect, there is no distillation column in this embodiment. The evaporated material passes directly to the side channel where it is immediately distilled.

There is no need for a distillation column as such in the present embodiment. The efficiency of the condensation tube described greatly exceeds that of the same length of smooth copper coil used before because its ribbing affords approximately double the surface area per unit of running length for the precipitation of the alcohol, and can be as much as six times the total area available for condensation for the same length of unit because of its wider diameter. The use of heat resistant connectors also isolates the condensation tube from heat sources maximizing its efficiency into a short space. It has been shown (e.g., by Blume, supra), that short efficient condensation devices are adequate rather than the high-ratio tall distillation columns familiar with high yield batch processors, especially for low yield production.

The distillation process, according to one aspect, automatically renders the fuel unfit for human consumption by using a rendering material in the alcohol distillation portion, which is more likely to make it acceptable for use in countries where alcohol consumption by humans is not socially acceptable or even not allowed. Only the alcohol is rendered unsafe for human consumption so that it can be used exclusively as a fuel, while the separated water produced by overflow from the flash evaporator is potable.

A small simple unit is inexpensive to build, easier to deliver to a work site, and to operate and maintain. Also, the small size of the unit means it is easier to store on site an entire spare unit for emergency replacement without depending upon a just-in-time inventory supply chain, which is nearly impossible to operate in remote field settings. Its small footprint also takes less energy to operate. If something goes wrong with the unit, it is easier to replace the modularized unit that has had attention given to human engineering principles in its construction, than one without such attention, so there is minimum loss of production time during replacement. The apparatus simplifies, modularizes, and concentrates the most important procedure of evaporation and distillation into a smaller workspace and sets it aside in an isolated position relative to the fuel generation apparatus. An added feature is the opportunity for preheating of the incoming fluid to be evaporated as it passes through the feed tube directed through the chimney of the heating device. This embodiment provides a simpler and more direct method of evaporating and distilling the alcohol from the mash than prior art, and it does so in a continuous stream utilizing low energy levels.

The feedstock used in one aspect can be processed to produce biodiesel that meets the D-6751 specification described in the Biodiesel Technical Manual. The mechanism and systematic process is described for a transformation of algae oil through alcoholysis (i.e., the breaking of a carbon to carbon bond by the addition of an alcohol), often referred to as transesterification (i.e. the process of exchanging the alcohol group of an ester with another alcohol). Ethanol is used in order to separate the fatty acids from the glycerol by replacing the glycerol with short linear alcohols. There are many known recipes. None of these use waste products exclusively as does the apparatus and procedure of the present embodiment.

Biodiesel consists of short chain alkyl or ethyl esters, typically made by transesterification of vegetable oils or animal fats, which can be used alone, or blended with conventional petrodiesel (petroleum diesel) in unmodified diesel engines. The process generally uses an acid-catalyzed esterification (i.e., conversion to an ester) followed by a base catalyzed transesterification. An acid of any of many varieties from agricultural waste, such as lemon juice from waste non-market quality harvest, old wine that has turned to vinegar, or the natural result of ethanol production, can be used as the acid catalyst. Ethyl alcohol produced by the fermentation of the same feedstock can be used as the alcohol. This is followed by using a base catalyst such as ashes from a wood fire for potash. However these ingredients are not a limitation and other ingredients can be used in their place. The key is that all operations are from locally collected agricultural, water, and mining waste products.

There have been, and continue to be, many recipes for biodiesel using ethanol since the process was first described by Chavanne in 1937. The procedure consists of several stages. First, oil comprised of triglycerides and free fatty acids (feedstock), an acid, and ethanol are reacted to form ethyl esters and triglycerides. The acid can be sulfuric acid, although virtually any acid such as vinegar, lemon juice, and the like will work as well. Second, a base is added to the ethyl esters and triglycerides. The base can be sodium hydroxide, potassium hydroxide (potash), calcium chloride, sodium methylate, potassium or sodium ethoxide, and the like. This leaves ethyl esters, glycerin, and trace contaminants. The glycerin can be removed by drainage through an outlet. In order to meet government standards, all of the glycerol alcohol, trace amounts of reaction catalysts, and water must be removed from the biodiesel before its use as a fuel. Diesel Number 2 can be purchased commercially and is essentially Heating Oil Number 2. If used as a heating oil locally it may not need to be cleaned to U.S. Government standards required for commercial sale to be used in wheeled transportation vehicles. If required, a centrifuge can be used to remove the trace contaminants from the ethyl esters, thereby leaving a final biodiesel product.

Other fats and oils besides those of algal origin can be used alone or in combination as feedstock. Other alcohols than ethanol can be used. Throughout this description, the expression plant and animal lipids, oils, or fats, denotes in general a generic designation of type of biological product, which may include products from any number of various species in all forms and colors. The material brought to the processing unit can be algae oil and be from any percentage of various species of algae by weight or volume.

Other benefits available to the producer of energy from algae include carbon credits which are marketable commodities traded on the Chicago Climate Exchange (CCX) and other places. Carbon credits require standardized records to be maintained for audit by the agency certifying their validity. These requirements are more easily met with standardized modules as complete independent systems that can each be operated by a single person, rather than by a number of more complex unique production systems. In a remote area with perhaps 100 villages, each could have its own standardized apparatus, which would make the reporting duties of the local officials standardized and easier to audit for compliance by outside compliance officers. The standardization of the modularized production units is a key to the implementation of the alternative energy system in a remote off-grid setting.

Algae live and thrive by taking carbon, oxygen, hydrogen, and nitrogen, from their environment, in combination with sunlight, to make their proteins, lipids, and carbohydrates. As they respire, algae take in $CO_2$, discard $O_2$, and keep the C. When algae die, their remains, made up of complex molecules formed as they grew, are decomposed by different organisms and returned to the soil, water, and the air. In anaerobic (i.e., oxygen starved) places such as a biogas generator or in swamps and bogs, the algae remains can be biodegraded by anaerobic microorganisms, such as bacteria, in an airless environment. Anaerobic microorganisms produce little heat and leave most of the energy which was locked up in their molecules as methane, $CH_4$. In contrast, in a compost pile exposed to open air, aerobic (i.e. those that require free oxygen for respiration) microorganisms produce temperatures as high as 70° C. (160° F.) and little methane.

House, supra, explains that the mechanism of methane production is still largely uncertain. It is hypothesized that numerous micro-organisms, similar to bacteria, including but not limited to mold, can prepare algae cell walls for destruction by other methane producing micro-organisms. It is further hypothesized that under the proper conditions in a biogas generator, also known as a digester, complex molecules are broken apart, step by step, into simpler molecules. It is further hypothesized that digestion is a form of disassembly line where one group of bacteria works on a complex molecule, derives energy from it and gives the separate parts, which are less complex molecules to another group of bacteria, that disassemble them further gaining energy themselves, and so on to the final group of bacteria that break the molecules into the very simplest molecules possible under the anaerobic circumstances primarily $H_2O$, $CO_2$, and $CH_4$.

Investigators agree that it takes different kinds of bacteria, each operating under different environmental conditions, to accomplish the complete disassembly of a complex molecule. According to White, supra, the methane producing micro-organisms, or methanogens, seem to be able to operate under a variety of special circumstances, and even to thrive under narrow ranges of temperatures and pH. The methanogens are a unique class of anaerobic bacteria. They derive energy by reducing carbon dioxide to methane, a quite different approach than other organisms. They use carbon dioxide as an energy source rather than treating it as an energy-depleted waste product. The methanogens are also special in that they can oxidize hydrogen gas. It is important to note that these organisms incorporate their carbon into the well known Krebs cycle for processing into amino acids, nucleic acids, and sugars. The respiratory pathway may have many variations, but they all build on the same backbone.

Digestion appears to occur in stages: aerobic (free) oxygen will inevitably enter any processing apparatus with the feedstock put into the methane digester, and these aerobic bacteria quickly exhaust any supply of oxygen, while doing what they can to break the feedstock materials down. $CO_2$ is released and some heat is generated. Then with the free $O_2$ gone, anaerobic bacteria thrive and release enzymes that attack large molecules that are still outside their own bodies (i.e., extracellular), so these molecules will be broken down into smaller sizes. The smaller size molecules are absorbed by microorganisms that resemble bacteria and are digested. The main byproducts of this reduction process are simple molecules such as short chain fatty acids, $H_2$ and $CO_2$. The hydrogen gas does not often show up in the final biogas because, it is hypothesized, that it is used by the anaerobic bacteria in the next stage in making $CH_4$, methane. The fatty acids are now altered by the last group of micro-organisms that resemble bacteria, which turn them primarily into $H_2O$, $CO_2$, and $CH_4$.

For general purposes, it is convenient to talk about biogas production as if it had only two stages, acid digestion and gas digestion, and as if there were only two groups of micro-organisms resembling bacteria involved, acid forming and methane forming. The second group is called methane forming, or methanogenic, even though they also produce other byproducts, because these microorganisms produce the methane component of biogas.

Ulrich Bretscher, supra, claims the speed of digestion of biomass materials is limited solely by the speed of hydrolysis (i.e., decomposition involving the breaking of a bond and the addition of the H and OH of water) of its solid matter. He suggests that after hydrolysis, the methanization (i.e., the forming of methane) occurs within minutes. A variety of factors affect the rate of digestion and biogas production. The most important is temperature. In theory, anaerobic bacteria communities can endure temperatures ranging from below freezing to above 57.2° C. However, the process is highly sensitive to disturbances, such as changes brought about by the introduction of additional feed materials. The temperature should remain relatively constant for the duration of digestion, which may be only two days, and there must exist within the digester the seed bacteria that can survive at that level, according to Ulrich Bretscher.

Other factors affect the rate and amount of biogas output. These include pH, water/solids ratio, carbon/nitrogen ratio, mixing frequency of the digesting material, the particle size of the material being digested, and retention time in the digester. Pre-sizing the biomass particle size by shredding and mixing occasionally, say every fifteen minutes, of the feed material for a uniform consistency allows the bacteria to work more quickly. Chemical materials can be added to maintain a consistent pH. It may be necessary to add water to the feed material if it is too dry. A carbon/nitrogen ratio of 20/1 to 30/1 is best. Retention time needed for a suitable level of digestion depends upon all of the above factors.

Methane gas is the major component of the natural gas used in many homes for cooking and heating. It is odorless, colorless, and yields about 9,000 kilocalories (kcal) of heat energy per cubic meter when burned. A cubic meter of biogas, also known as sour gas, comprising $CH_4$, $CO_2$, $H_2O$ (as a vapor), and sometimes $N_2$ (gas), $H_2S$ (hydrogen sulfide gas), $H_2$ (gas) and minute traces of other gases, yields about 90 kcal for each percent content of methane. For example, biogas composed of 65% methane yields 5,857 kcal/cubic meter.

Biogas produced in anaerobic digesters can have widely varying yields such as methane (50%-80%), carbon dioxide (20%-50%). The relative percentage of these gases in biogas depends on the nature, health, and nutritional state of the feedstock material, and management of the process. A requirement of producing methane is to make sure the pH and temperature stay in a comfortable range for the bacteria. If the pH of the slurry is below 6.8 the production slows, and at 5.5 pH the methane-forming bacteria can stop functioning completely.

In a typical instance, the initial recovery of biogas from algae will produce a combination of about 65% methane, and the rest primarily carbon dioxide and trace gases. If allowed to sit undisturbed long enough, the carbon dioxide component of biogas will settle to the bottom of a gas storage container. To hasten separation, referred to as scrubbing the methane, and make it approach pipeline, i.e., usable, quality, it is typically run through a scrubber. Countless variants have been tried, most of which are expensive. It is common to hear that it is more expensive to buy the equipment to scrub the gas than to buy the electrical generating equipment to produce electricity that runs on that fuel. Prior research suggests that to increase the purity of the methane by about 15 percent would require passing the sour gas through approximately a three-meter (ten-foot) depth of water, if available, as a low cost and rather unsophisticated alternative, according to Blume.

Conclusions, Ramifications, and Scope

Accordingly the reader will see that, according to one or more aspects, we have provided a system and method for the production of biofuels including methane, ethanol, and biodiesel. These fuels are selectively produced by controlling conditions, including temperature, pH, and other chemical compositions in the reaction tank. The chemical conditions are controlled through periodic sampling, testing, and adjusting during breakdown of the algae. The methane produced by the process is sufficient to power a generator and all pumps, and to provide burnable fuel for the burners used in heating the main reaction tank and still. A battery is used in conjunction with the generator to store left-over electrical energy for later use. The ethanol and biodiesel can be sold or used as fuels for other needs. The system is relatively inexpensive and can be operated independently in remote areas by relatively unskilled operators. The $CO_2$ that is generated and held can be traded for carbon credits.

While the above description contains many specificities, these should not be construed as limitations on the scope, but as exemplifications of some present embodiments. Many other ramifications and variations are possible within the teachings.

For example, although the specific dimensions can be varied within the scope of this apparatus, they have been given to illustrate that the overall size of the fully functional compact unit can fit on a mobile platform sized to fit on a trailer chassis with the expansion of the gas bags away and out to the side, and the scrubber's water reservoir filled at the remote location.

Multiple units, under one embodiment, would be made by providing three containers, each for a different cycle in fuel production rotation. Because methane production is correlated with internal temperature, full cycles can be completed in as little as three days if the choice is made to bypass ethanol production. With multiple units, some might produce ethanol and others only methane. Others can be devoted to biodiesel production. Because of the payments for the carbon credits, methane is a desirable fuel. If all three fuel operations are bypassed, the evaporator and distillation device can be devoted to the production of potable water.

The apparatus according to one aspect uses only self generated power, i.e., achieves true energy self sufficiency which is a very desirable feature at any off-grid site and especially at a remote site that could not possibly have grid access. The reduction of waste from other operations, such as the production of biodiesel fuel, is a major feature of the present apparatus. The waste reduction may include recycling water, using debris from local mining operations, and even converting other agricultural waste to fuel. It is potentially possible to qualify for an additional income stream by receiving carbon credits by sequestering the carbon dioxide that is produced along with the production of the biofuel. The carbon dioxide is produced during ethanol fermentation and during methane digestion. However produced, it can be captured, scrubbed in recycling water, and used for other agriculture activities such as encouraging the growth of more feedstock algae in the originating pond. The sequestering of carbon dioxide and its recycling within the ecological system is a major payoff to the apparatus and method.

Cleaned methane gas can be held in storage and released under appropriate conditions to provide fuel for electricity generation or for release as scrubbed bio-gas to the pipeline grid, if one is available, since after cleaning it resembles commercial pipeline quality natural gas. It could also be used in other activities such as powering a higher end electrical generating apparatus that supplies power to the grid, if that choice is available, or to storage batteries for use through an inverter during electrical generation quiet times. That use either real time or from battery storage can power separate production equipment which is not part of this apparatus, but because it can be located in the same physical plant as the biofuel production apparatus, can be operated by the same person.

In this apparatus, which does use a shallow recirculating water source, the sour gas methane is forced through a bubbler past rechargeable temporary absorption material which is locally collected calcium carbonate waste (limestone debris from a quarry) thus reducing the amount of time, water, expense, and space required to scrub a portion of the carbon dioxide. A key feature of the scrubber of this apparatus is that it is recharged by flushing with water from an algae feedstock growing pond, which both freshens the scrubber, and adds the $CO_2$ to the growing environment to encourage more algae feedstock growth. Carbon dioxide produced during either ethanol fermentation or methane digestion is captured and processed through the same scrubber. Records of such scrubbing are credited toward the carbon credit account.

An additional feature of this apparatus is that the continuous processing evaporator and distillation unit can be fed by multiple and separate fermentation units, which may feed the ethanol-water temporary holding tank. Thus, there could be multiple fermentation units feeding just the one evaporation apparatus, which might run continuously.

While the present system employs elements which are well known to those skilled in the arts of biofuel process design, it combines these elements in a novel way which produces new results not heretofore discovered. Accordingly the scope of this invention should be determined, not by the embodiments illustrated, but by the appended claims and their legal equivalents.

The invention claimed is:

1. A method for selectively producing a biofuel from algae, comprising:
   (a) providing a sealed reaction tank with a lid, said lid being removable and arranged to effect an airtight seal of said tank when installed on said tank,
   (b) providing said tank with a sampling and adjusting tube having two ends, an outer end and an inner end, said tube extending downward into said tank so that said outer end is outside said tank and said inner end is inside said tank, said inner end being open, said outer end containing an airlock for
      (i) allowing fluid to pass from said tank through said tube out through said airlock to permit sampling of the contents of said tank, and
      (ii) preventing air from entering said container via said airlock and said tube,
   (c) providing at least one storage container,
   (d) providing a conduit for passage of gas between said reaction tank and said storage container,
   (e) providing a stirrer for stirring the contents of said tank,
   (f) providing a supply of algae,
   (g) providing a supply of a seed substance selected from the group consisting of bacteria and yeast,
   (h) providing temperature-control means for said reaction tank,
   (i) providing a source of water,
   (j) adding a quantity of water, said supply of algae, and said supply of said seed substance to said reaction tank to provide a liquid feedstock mixture in said tank,
   (k) attaching said lid to said tank to seal said tank,
   (l) using said temperature control means to establish a temperature within said reaction tank that is suitable for said bacteria or yeast to act on said liquid feedstock mixture to produce a biofuel selected from the group consisting of methane, ethanol, and biodiesel,
   (m) activating said stirrer to stir said contents of said tank,
   (n) obtaining a sample of said feedstock mixture from said tank through said sampling and adjusting tube,
   (o) analyzing at least one condition of said feedstock mixture obtained via said tube, said condition selected from the group consisting of chemical composition, nutrient level, and pH,
   (p) if said condition is outside a predetermined tolerance range, then adjusting the composition of said feedstock mixture by adding a substance to said feedstock via said sampling and adjusting tube in order to maintain said condition of said feedstock within said predetermined tolerance range without allowing oxygen to enter said tank,
   (q) collecting said biofuel in said storage container,
   whereby a biofuel will be produced from said algae said biofuel can be transferred to said storage container, and said feedstock mixture in said tank can be monitored and adjusted without admitting oxygen-containing ambient air into said tank.

2. The method of claim 1, further including powering said temperature-control means by said biofuel.

3. The method of claim 1 wherein said temperature control means is set to provide a sufficiently high temperature so as to produce methane from said algae.

4. The method of claim 1 wherein said temperature control means is set to provide a sufficiently low temperature so as to produce ethanol from said algae.

5. The method of claim 1 wherein said seed substance is yeast and said biofuel is ethanol.

6. The method of claim 1, further including:
   providing a still with a condensing tube,
   providing heating means for said still,
   providing a conduit from said reaction tank to said still,
   providing a valve in said conduit,
   using said temperature control means to establish a temperature within said reaction tank that is suitable for said production of ethanol within the mixture comprising said water, said algae, and said seed substance, and after producing said ethanol, heating said still using said heating means, opening said valve in said conduit, and allowing said feedstock mixture from said tank to enter said still,
   whereupon said ethanol will vaporize and leave said still via said condensing tube so that said ethanol vapor will condense and flow into a container for storage and later use.

7. The method of claim 6 wherein said condensing tube is thermally isolated from the remainder of said still.

8. The method of claim 6 wherein said condensing tube is made from materials selected from the group consisting of copper and aluminum.

9. The method of claim 1, further including:
   providing a scrubber containing carbonate material for scrubbing said gas and having an entrance and an exit, said entrance comprising a bubbler tube, said exit comprising a port selected from the group consisting of a port connected through a valve to a storage container for scrubbed gas, and a port connected through a valve to a vent for said scrubbed gas,
   providing a source of water for said scrubber and filling said scrubber to a predetermined level with water from said source,
   supplying said entrance with said gas, and causing said gas to bubble through said carbonate material and said water,
   allowing said scrubbed gas to leave said scrubber through said exit,
   whereby said gas enters said entrance, is scrubbed by said carbonate material, and leaves through said exit.

10. The method of claim 9, further including using said scrubber to scrub sour methane gas in order to obtain carbon credits.

11. The method of claim 1 wherein said stirrer comprises at least one paddle within said reaction tank and a motive source for moving said paddle.

12. The method of claim 1 wherein said sampling and adjusting tube extends through said lid of said tank.

13. The method of claim 1 wherein said analyzing measures the pH of said mixture and adjusting the pH and temperature of said mixture comprising said algae, said water, and said seed substance in order to indicate a condition selected from the group consisting of whether any sugars within said algae are exhausted in conversion to alcohol and whether the pH of said mixture has become too low for said yeast to thrive.

14. A method for producing biodiesel from algae, comprising:
   (a) providing a reaction tank with a sealable and removable lid, said lid arranged to effect an airtight seal of said tank when installed on said tank, and
   a mechanical stirrer with a motive source for actuating said stirrer,
   (b) providing said tank with a sampling and adjusting tube having two ends, an outer end and an inner end, said tube extending downward into said tank so that said outer end is outside said tank and said inner end is inside said tank, said inner end being open, said outer end containing an airlock for
- (i) allowing fluid to pass from said tank through said tube out through said airlock to permit sampling of the contents of said tank, and
- (ii) preventing air from entering said container via said airlock and said tube, (c) providing a supply of a naturally lipid and carbohydrate-containing algae, (d) providing a supply of yeast, (e) providing a temperature-control means for said reaction tank, (f) providing a source of water, (g) adding said water, said algae, and said yeast to said reaction tank to provide a liquid feedstock mixture in said tank, (h) using said temperature control means to establish a temperature within said reaction tank that is suitable for said yeast to cause fermentation of said algae in order to produce ethanol, (i) stirring said mixture until said fermentation stops, (j) sampling said mixture in said tank via said sampling and adjusting tube and analyzing said mixture to monitor said feedstock mixture in said tank and (k) if said condition is outside a predetermined tolerance range, then adjusting the composition of said feedstock mixture by adding a substance to said feedstock via said sampling and adjusting tube in order to maintain said condition of said feedstock within said predetermined tolerance range without allowing oxygen to enter said tank, (l) adding a base material to said mixture via said sampling and adjusting tube to cause transesterification of said mixture to produce biodiesel and glycerin, and (m) allowing said biodiesel and glycerin to separate while at rest within said tank and removing said biodiesel from said reaction tank, whereby said algae is used to produce biodiesel and said feedstock mixture in said tank can be monitored and adjusted without admitting oxygen-containing ambient air into said tank.

15. A method of producing a biofuel selected from the group consisting of methane gas, ethanol, or biodiesel, comprising:
- (a) providing a reaction tank having a sealed lid, wherein said lid is a removable lid and arranged to affect an airtight seal of said tank when installed on said tank,
- (b) providing said tank with a sampling and adjusting tube having two ends, an outer end and an inner end, said tube extending downward into said tank so that said outer end is outside said tank and said inner end is inside said tank, said inner end being open, said outer end containing an airlock for
    - (i) allowing fluid to pass from said tank through said tube out through said airlock to permit sampling of the contents of said tank, and
    - (ii) preventing air from entering said container via said airlock and said tube,
- (c) providing a storage container,
- (d) providing a feedstock of algae in said tank,
- (e) providing temperature control means for said tank,
- (f) adding a seed material selected from the group consisting of bacteria and yeast to said tank to produce a feedstock material comprising said algae and said seed material,
- (g) using said temperature control means to establish a predetermined temperature within said tank so that said seed material will cause said feedstock to ferment in order to produce a biofuel selected from the group consisting of methane, ethanol, and biodiesel,
- (h) said feedstock mixture in said tank to be monitored by obtaining a sample of said feedstock mixture from said tank through said sampling and adjusting tube,
- (i) analyzing at least one condition of said feedstock mixture obtained via said sampling and adjusting tube, said condition selected from the group consisting of chemical composition, nutrient level, and pH,
- (j) if said condition is outside a predetermined tolerance range, then adjusting the composition of said feedstock mixture by adding a substance to said feedstock via said sampling and adjusting tube in order to maintain said condition of said feedstock within said predetermined tolerance range, without admitting oxygen-containing ambient air into said tank,
- (k) thereby to produce a biofuel from algae and store said biofuel within said container and enabling said feedstock mixture in said tank to be monitored and adjusted without admitting oxygen-containing ambient air into said tank.

16. The method of claim 15, further including:
providing a still connected to said tank,
distilling the contents of said tank when said biofuel is ethanol,
whereby ethanol can be collected in a container and water can be drained from the still.

* * * * *